US012733989B2

(12) United States Patent
Krishnan et al.

(10) Patent No.: US 12,733,989 B2
(45) Date of Patent: Sep. 15, 2026

(54) SYSTEMS AND METHODS FOR IDENTIFYING ANATOMICAL LANDMARKS INSIDE A HUMAN BODY FOR PLACEMENT OF A MEDICAL DEVICE

(71) Applicants: Subramaniam C. Krishnan, Sacramento, CA (US); Arvind SC Krishnan, Sacramento, CA (US)

(72) Inventors: Subramaniam C. Krishnan, Sacramento, CA (US); Arvind SC Krishnan, Sacramento, CA (US)

( * ) Notice: Subject to any disclaimer, the term of this patent is extended or adjusted under 35 U.S.C. 154(b) by 0 days.

(21) Appl. No.: 18/736,383

(22) Filed: Jun. 6, 2024

(65) Prior Publication Data

US 2024/0407855 A1 Dec. 12, 2024

Related U.S. Application Data

(60) Provisional application No. 63/471,381, filed on Jun. 6, 2023.

(51) Int. Cl.

| | |
|---|---|
| ***A61B 34/20*** | (2016.01) |
| ***A61B 6/00*** | (2024.01) |
| *A61B 90/00* | (2016.01) |

(52) U.S. Cl.

CPC .............. *A61B 34/20* (2016.02); *A61B 6/481* (2013.01); *A61B 2090/376* (2016.02)

(58) Field of Classification Search

CPC .... A61B 34/20; A61B 6/481; A61B 2090/376

See application file for complete search history.

(56) References Cited

U.S. PATENT DOCUMENTS

| | | | | |
|---|---|---|---|---|
| 2010/0210938 A1* | 8/2010 | Verard | .................. | A61B 6/463 600/424 |
| 2020/0179050 A1* | 6/2020 | Walsh | .............. | A61M 25/0067 |

* cited by examiner

*Primary Examiner* — Chao Sheng

(74) *Attorney, Agent, or Firm* — Snell & Wilmer LLP

(57) ABSTRACT

A method for identifying an anatomical landmark inside a human body for lead fixation of a medical device. One or more balloons are inflated using air or fluid. A delivery sheath having a distal end attached to the one or more balloons is advanced across a tricuspid valve to a right ventricle. A moderator band or an anterior papillary muscle is identified by the one or more balloons, using X-ray or fluoroscopy. The one or more balloons is then moved to be adjacent to a smooth portion of an inlet septum using the delivery sheath or inflation of the one or more balloons. Using X-ray or fluoroscopy, compression or deformation of the one or more balloons is visualized when an outer curvature and/or a distal pole of the one or more balloons contacts the inlet septum. Using a lumen of the delivery sheath, a lead of a medical device is advanced into the inlet septum.

19 Claims, 12 Drawing Sheets

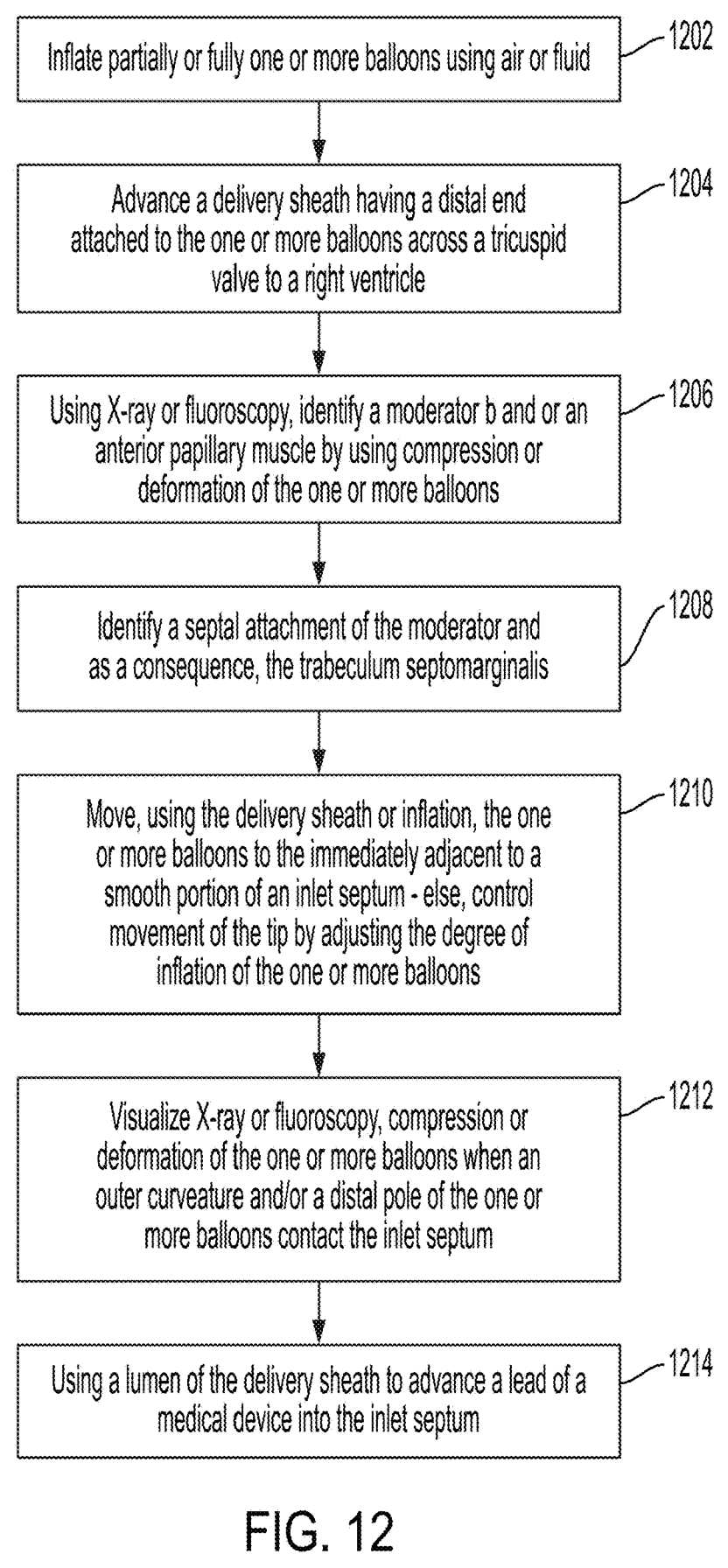

Inflate partially or fully one or more balloons using air or fluid — 1202

Advance a delivery sheath having a distal end attached to the one or more balloons across a tricuspid valve to a right ventricle — 1204

Using X-ray or fluoroscopy, identify a moderator b and or an anterior papillary muscle by using compression or deformation of the one or more balloons — 1206

Identify a septal attachment of the moderator and as a consequence, the trabeculum septomarginalis — 1208

Move, using the delivery sheath or inflation, the one or more balloons to the immediately adjacent to a smooth portion of an inlet septum - else, control movement of the tip by adjusting the degree of inflation of the one or more balloons — 1210

Visualize X-ray or fluoroscopy, compression or deformation of the one or more balloons when an outer curveature and/or a distal pole of the one or more balloons contact the inlet septum — 1212

Using a lumen of the delivery sheath to advance a lead of a medical device into the inlet septum — 1214

FIG. 12

SYSTEMS AND METHODS FOR IDENTIFYING ANATOMICAL LANDMARKS INSIDE A HUMAN BODY FOR PLACEMENT OF A MEDICAL DEVICE

CROSS-REFERENCE TO RELATED APPLICATION

This application claims the benefit and priority to U.S. Provisional App. No. 63/471,381, filed on Jun. 6, 2023, entitled "Technology to Define Cardiac Anatomy Better & Improve Implantation of Left Bundle Pacing Leads," the entire contents of which is hereby incorporated by reference in its entirety for all purposes.

BACKGROUND

1. Field of the Invention

The invention relates to systems and methods for identifying anatomical landmarks inside a human body for placement of a medical device, and more specifically, to systems and methods for identifying anatomical landmarks inside a human body for guiding cardiac procedures.

2. Description of the Related Art

Many different medical procedures have been used to implant medical devices (e.g., pacemakers). As an example, conductive system pacing (CSP) has been used over the past 2 decades. CSP is a technique that involves implantation of permanent leads along different sites of the cardiac conduction system. CSP focuses on overcoming sites of atrioventricular (AV) conduction slowing or conduction block to provide a pacing solution that results in more synchronized biventricular activation. The lead placement for CSP can be targeted at the bundle of His, known as His bundle pacing (HBP) or at the region of the left bundle branch (LBB), known as LBB pacing (LBBP).

Initially, HBP provided the most physiological ventricular electrical activation with a high success rate. However, the high pacing threshold seen with this technique worsens over time. In addition, the size of the electrical signal recorded or sensed, i.e., the R wave amplitude, also tends to be low. Hence, recently, left bundle area pacing (LBAP) has emerged as an alternative mode of CSP.

Currently, all techniques for inserting the LBBP pacing lead require the use of a delivery sheath, most often with a preformed curve, sometimes with the ability to adjust the curve. For example, the delivery sheath is advanced across a tricuspid annulus and positioned against an interventricular septum. The positioning of the LBBP lead deep into the interventricular septum is confirmed with fluoroscopy. The use of fluoroscopy alone, is difficult since it is hard to visualize anatomical landmarks to further guide the pacing location. A key feature of implanting pacemaker leads at precise locations is the requirement for recognizing anatomical landmarks such as the His bundle or the mitral or tricuspid valve annulus during the procedure. For example, placing a left bundle pacing lead requires recognizing the location of the His bundle location, the right ventricular apex, etc. The His bundle is typically located at the superior and septal portion of the tricuspid valve annulus. Placing a catheter within the coronary sinus, a structure which can serve as a surrogate marker of the tricuspid annulus and thus be recognized with fluoroscopy. In addition, the use of real-time ultrasound imaging is also possible for recognizing anatomical landmarks. Similarly, placing a catheter to identify the His bundle electrogram and thereby the superior septal tricuspid annulus is also possible but, again, impractical. Hence, the routine of these technologies is not practical, not accurate and very expensive.

Furthermore, lead-induced tricuspid regurgitation (TR) is one potential complication of LBBP. That is, with LBBP, a potential risk of causing or worsening TR exists since the lead crosses the tricuspid septal valve leaflet and is fixed deep into the interventricular septum near the valve annulus. In one particular study, TR was caused or worsened by LBBP lead implantation in over 11% of the patients.

Various other methods have been developed to more safely and accurately guide LBBP implantation. For example, using echocardiography has been used to determine where to implant a medical device, for example, a pacemaker. As compared to fluoroscopy, echocardiography can be used to clearly visualize the valve annulus and accurately measure the distance between the implanted site and the valve annulus. However, once again, the use of echocardiography to guide a medical device implantation is not practical.

Therefore, there is a need for safer and more accurate systems and methods to identify anatomical landmarks inside a human body for guiding cardiac procedures.

SUMMARY

Aspects disclosed herein include a method for identifying an anatomical landmark inside a human body for lead fixation of a medical device. One or more balloons are inflated using air or fluid (or the one or more balloons can be prefilled with air or fluid). In various aspects, the tip at the distal end of a catheter shaft has a maximum radial dimension that is larger than the radial dimension of the catheter shaft and is extremely deformable. In addition, the expandable portion may be present exclusively along the outer curvature of the delivery sheath or may have an asymmetric nature in that the diameter or radial dimension is larger along the outer curvature of the delivery sheath. A delivery sheath having a distal end attached to the one or more balloons is advanced across a tricuspid valve to a right ventricle. A moderator band (especially its septal attachment) or an anterior papillary muscle or the trabeculum septomarginalis is identified by the deformation of one or more balloons, using X-ray or fluoroscopy. The one or more balloons is moved to be adjacent to a smooth inlet septum using the delivery sheath or inflation of the one or more balloons. Using X-ray or fluoroscopy, compression or deformation of the one or more balloons is visualized when an outer curvature and/or a distal pole of the one or more balloons contacts the inlet septum. Using a lumen of the delivery sheath, a lead of a medical device is advanced into the inlet septum.

BRIEF DESCRIPTION OF THE DRAWINGS

These and other embodiments of the invention will be discussed with reference to the following exemplary and non-limiting illustrations, in which like elements are numbered similarly, and where:

FIG. 12 is a flowchart illustrating a method for identifying an anatomical landmark inside a human body for lead fixation of a medical device to illustrate various aspects of the invention.

DETAILED DESCRIPTION

Figure 1:
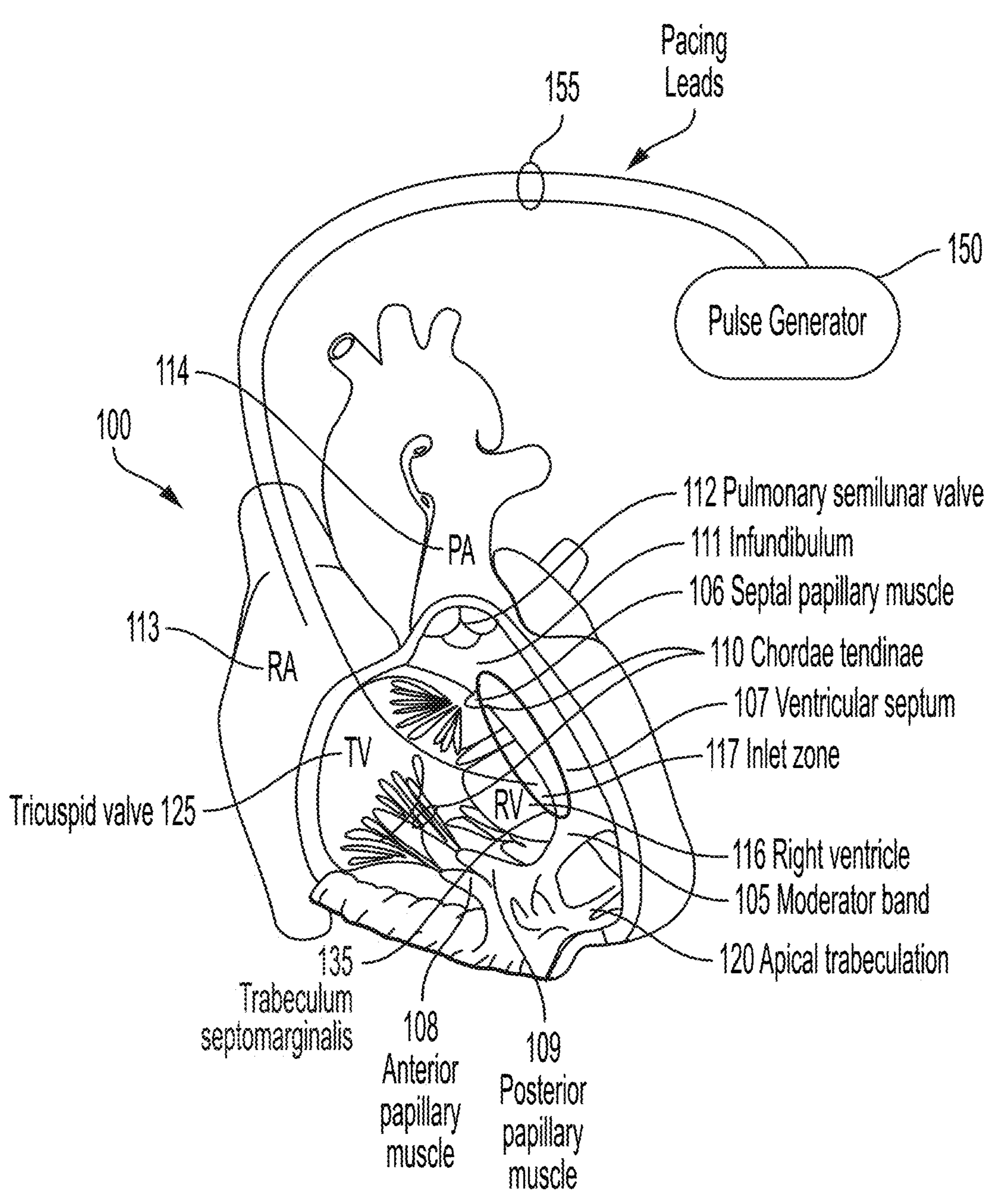
FIG. 1 is a perspective view of a portion of a patient's heart to illustrate various aspects of the invention.

FIG. 1 is a perspective view of a portion of a patient's heart 100 to illustrate various aspects of the invention. An interior aspect of a right ventricle (RV) 116 is shown after the free wall of the RV 116 is peeled off. FIG. 1 also shows a moderator band 105, which is a prominent muscle bundle that extends from a ventricular septum 107 (which continues up the interventricular septum 107 as the trabeculum septomarginalis 135 and laterally, by the free wall and an anterior papillary muscle 108). The moderator band 105 is an anatomical structure of the patient's heart 100 that separates an inlet component 114 of the RV 116 from an apical trabecular zone 120.

As shown in FIG. 1, the moderator band 105 is a highly prominent muscle bundle in the RV 116. The moderator band 105 originates from a ventricular septum 107 and extends to a base of an anterior papillary muscle 108. The moderator band 105 also provides support to the anterior papillary muscle 108, guides blood from the inflow tract to the outflow tract of the RV 116, and prevents RV overdistention, especially in cases of RV infraction. As shown in FIG. 1, the anterior papillary muscle 108 is positioned along the lateral extent of the moderator band 105. The moderator band 105 generally has a length of about 16.23 millimeters (mm)+/−2.3 mm and a thickness of about 4.5 millimeters (mm)+/−1.8 mm. The moderator band 105 is an anatomical landmark to guide positioning of a LB pacing lead. The tricuspid valve (TV) 125 is a complex anatomical structure that includes a saddle-shaped tricuspid annulus, asymmetric leaflets, and a subvalvular apparatus.

After the moderator band 105 is identified, an inlet septum 117 adjacent to the moderator band 105 is targeted for lead 155 fixation or placement of the medical device 150 (e.g., a pulse generator or a pacemaker). According to an aspect, one lead 155 is inserted into a right atrium 113 and one lead 155 is inserted into the inlet zone 117 of the RV 116. The concepts discussed in this invention also apply to "leadless pacemakers".

Figure 2:
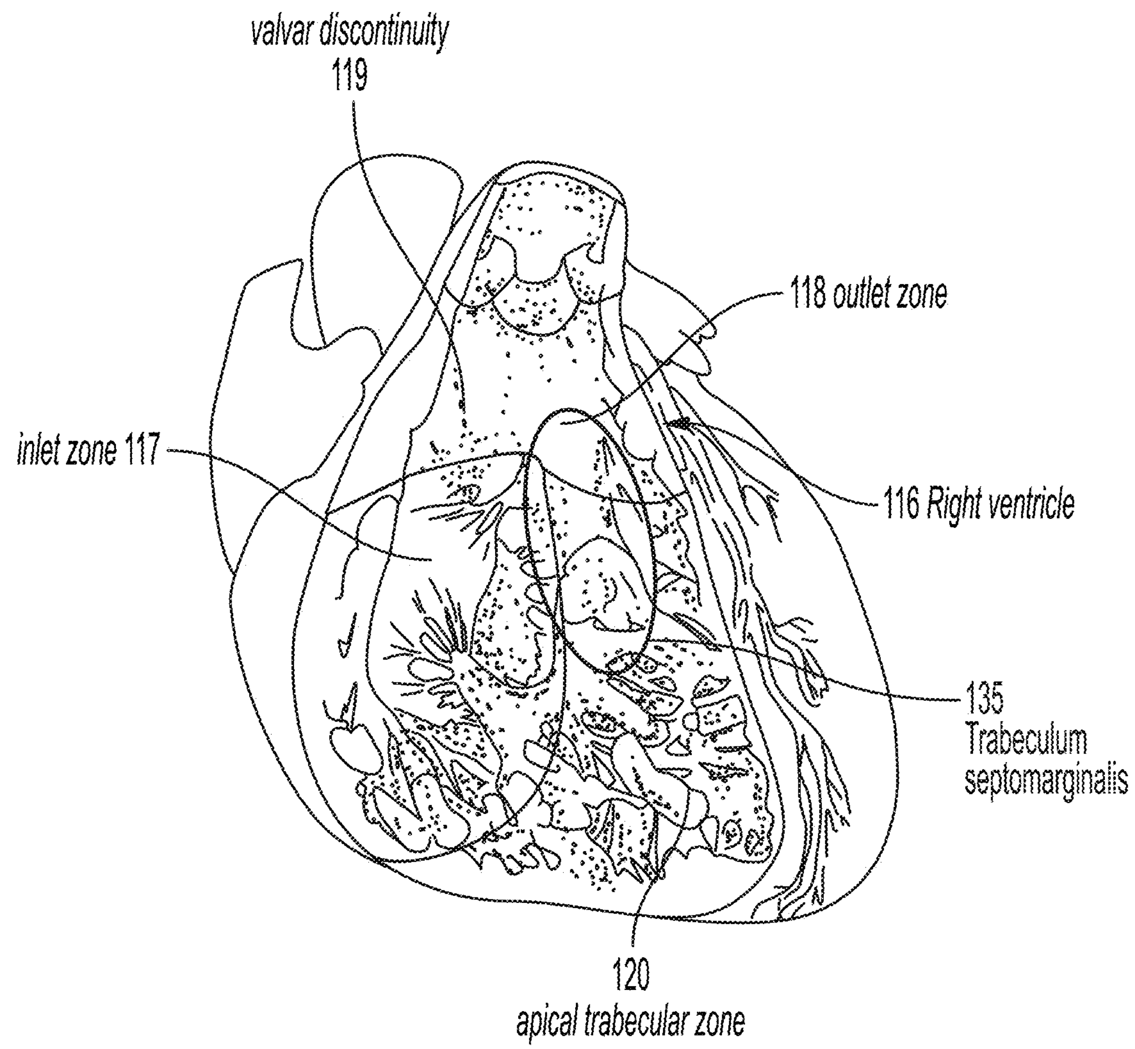
FIG. 2 is a plan view of the right ventricle to illustrate 3 different zones of the right ventricle (the inlet portion, the outflow tract and the apical trabecular zone) to illustrate various aspects of the invention.

FIG. 2 is a plan view of the right ventricle 116 to illustrate 3 different zones of the right ventricle 116 (the inlet zone 117, the outflow tract 118 and the apical trabecular zone 120) to illustrate various aspects of the invention. As shown, the 3 different zones include the inlet zone 117, the outlet zone or outflow tract 118, and the apical trabecular zone 120. Referring to FIGS. 1 and 2, the moderator band 105 separates the inlet zone 117 from the apical trabecular zone 120. The inlet septum 117 is smooth and lends itself to better medical device fixation, for example, pacemaker lead fixation. That is, the medical device 150 functions and performs better, more accurately, and more reliably when at least one of the leads 155 is affixed to the inlet zone 117. After the moderator band 105 is identified, the inlet septum 117 adjacent to the moderator band 105 is targeted for lead fixation or placement of the medical device 150. The trabeculum septomarginalis 135 which is a muscle bundle that runs along the septum and continues as the moderator band 105 can also be identified and used as an anatomical landmark to guide the lead implantation.

Figure 3:
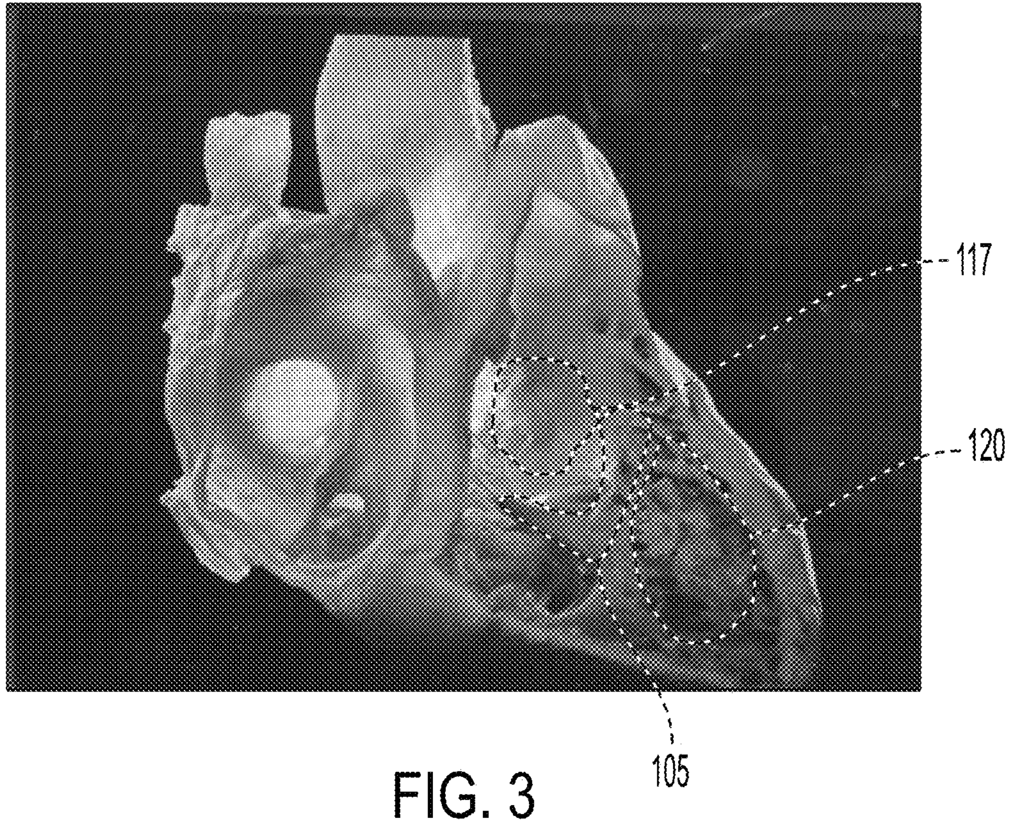
FIG. 3 is a photo of the ventricular free wall of the right ventricle removed to further illustrate the septal portion of the inlet zone, i.e., the inlet septum, and the septal portion of the apical trabeculation zone, i.e., the apical trabecular septum, to illustrate various aspects of the invention.

FIG. 3 is a photo of the ventricular free wall of the right ventricle removed to further illustrate the septal portion of the inlet zone 117, i.e., the inlet septum, and the septal portion of the apical trabeculation zone 120, i.e., the apical trabecular septum, to illustrate various aspects of the invention. The moderator band 105 clearly separates the inlet portion 117 of the right ventricle 116 from the apical trabecular septum 120. Unlike the apical trabecular septum 120, the inlet septum 117 is smooth and lends itself to attachment of the pacemaker lead 155. The moderator band 105 separates the inlet zone 117, which is smooth, from the apical trabecular septum 120, which is extremely uneven.

Figure 4:
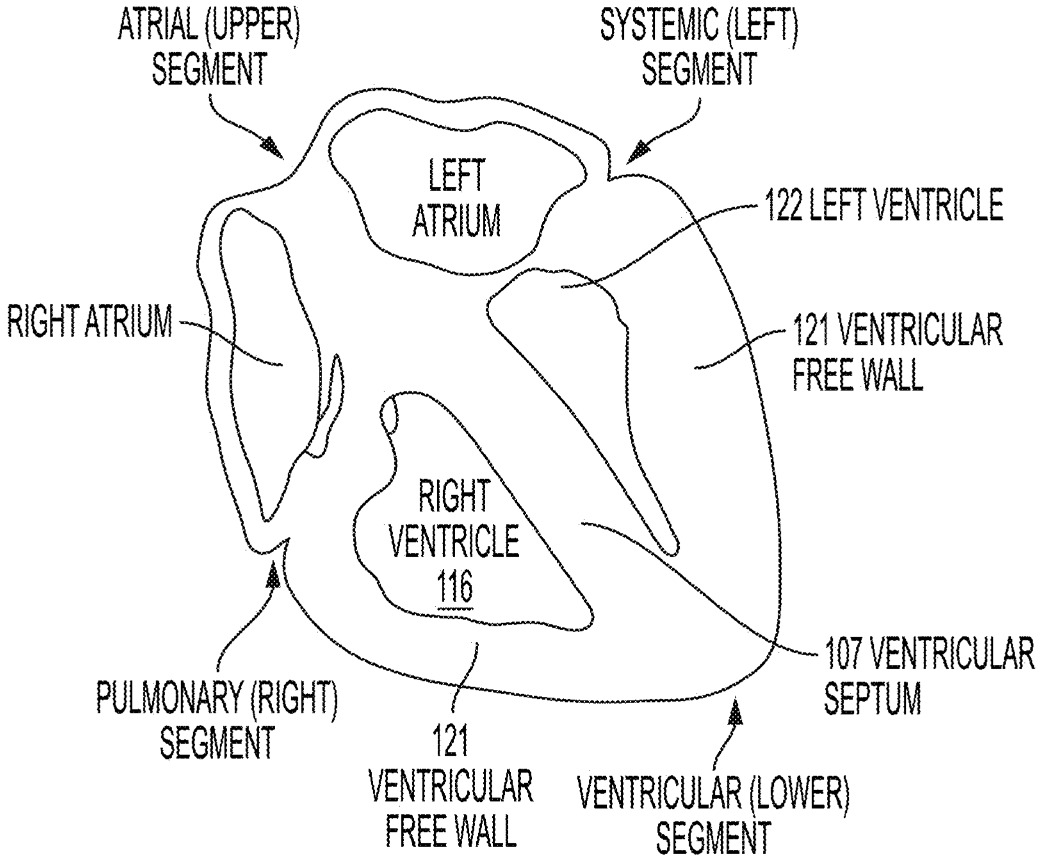
FIG. 4 is a plan view of a patient's heart showing the ventricular septum, the right ventricle, and the ventricular free wall to illustrate various aspects of the invention.

FIG. 4 is a plan view of a patient's heart showing the ventricular septum 107, the right ventricle 116, and the ventricular free wall 121 to illustrate various aspects of the invention. The ventricular septum 107 is a muscular partition that separates the right ventricle 116 from the left ventricle 122.

Figure 5:
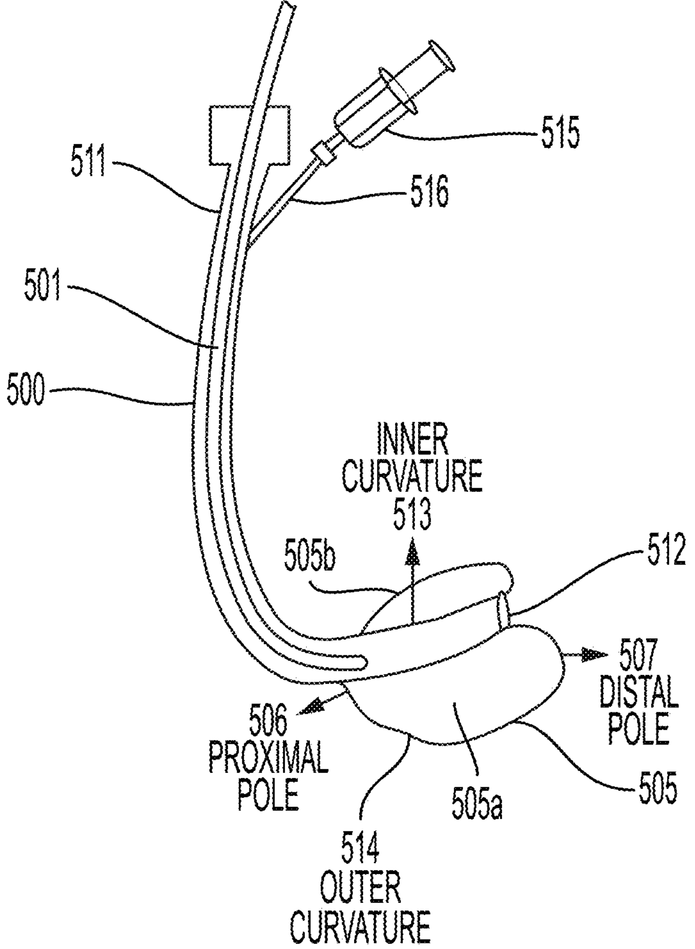
FIG. 5 is a plan view of a delivery sheath with an asymmetric distal portion i.e. balloon to facilitate insertion of a lead (e.g., a pacemaker lead) into the inlet septum to illustrate various aspects of the invention.

FIG. 5 is a plan view of a delivery sheath 500 with an asymmetric balloon 505 to facilitate insertion of a lead 155 (e.g., a pacemaker lead) into the inlet septum 117 to illustrate various aspect of the invention. The delivery sheath 500 can be used to guide a catheter 501 into the patient's body (e.g., into an artery or a vein). The delivery sheath 500 can also be used to protect the catheter 501. The delivery sheath 500 has a proximal end 511 and a distal end 512.

The proximal end 511 of the delivery sheath 500 has a separate lumen (can be more than one lumen) to allow for injection into the expandable component and into the lumen 516 to allow for insertion of a contrast dye fluid or air using a syringe 515 into the one or more balloons 505. Upon injection of air and/or fluid such as contrast dye fluid or radio-opaque contrast fluid, the asymmetrical balloon 505, located at the distal end 512 of the delivery sheath 500, gets inflated (either partially or fully). The contrast dye fluid or radio-opaque contrast fluid allow for visibility with fluoroscopy or echocardiography when inside the human body. The hyper or ultracompliant balloon 505 can be partially or fully inflated with air and/or fluid, thus advantageously allowing more accurate control of the lead for fixation or attachment to the inlet septum 117. The balloon 505 gets advanced using the delivery sheath 500 and/or the catheter 501 into the right ventricle 116 along the direction of blood flow.

The asymmetric shape of the balloon 505 advantageously allows for full inflation without damaging of the chordae tendinae 110, which is attached to the tricuspid valve 125 (see also FIG. 1). The asymmetry of the balloon 505 is with respect to the delivery sheath 500, i.e., the outer portion 505*a* is offset from and is larger than the inner portion 505*b*. The balloon 505 may also be a hemiballoon. The balloon 505 is made of a material that is very compliant, and deformable and that allows the balloon 505 to be visible within a human body when using X-ray or fluoroscopy or ultrasound imaging. When the balloon 505 is in contact with the myocardium, the ventricular septum 107, the moderator band 105 or other structures, the compression of the balloon 505 is readily apparent using X-ray or fluoroscopy or echocardiography, allowing for very precise and accurate identification of anatomical landmarks inside the human body. This ultimately results in the lead 155 being placed in a location that produces better results for the patient.

As shown, the balloon 505 is asymmetrical about the delivery sheath 500 such that the outer portion 505*a* of the balloon 505 is between about 65-90% in volume and the inner portion 505*b* of the balloon 505 is between about 10-35% in volume for a total volume of 100% when fully inflated. The outer portion 505*a* and the inner portion 505*b* can be portions of a single balloon or can be two separate hemispheric balloons. Generally, the outer portion 505*a* is larger in size and volume than the inner portion 505*b*. The balloon 505 also has a proximal end or pole 506 and a distal end or pole 507. Upon full inflation of the balloon 505, the distal pole 507 of the balloon 505 extends or protrude beyond the distal end 512 (i.e., end tip) of the delivery sheath 500 and therefore prevents trauma to the myocardium. By improving contact of the end tip 512 of the delivery sheath 500 with the myocardium, this prevents contrast leakage when the fluid is injected through the end tip 512 of the hollow tube or the delivery sheath 500. In various aspects, the inflated balloon 505 does not cover or encroach on the lumen (i.e., passageway) of the delivery sheath 500. This is to ensure that nothing (e.g., a screw or a helix) passing through the lumen to the distal end 512 punctures or traumatizes the balloon 505. Inflation or deflation of the one or more balloons 505 can help adjust the orientation of the delivery sheath 500 with respect to the ventricular septum 107.

The balloon's material or coating advantageously allows the balloon 505 to be seen using X-ray, fluoroscopy or ultrasound and the balloon's distal pole 507 of the outer portion 505*a* allows the balloon 505 to be adjusted to a correct and safe position adjacent to the inlet septum 117 and/or the moderator band 105 so the inlet septum 117 can be targeted for lead fixation or placement of the medical device via the delivery sheath 500. Since the balloon 505 is very compliant and deformable, the distal pole 507 of the balloon 505 can gently come into contact with the inlet septum 117 without damaging it. In some aspects, the outer portion 505*a* and/or the outer curvature 514 of the balloon 505 can abut, rest on or push against the moderator band 105, providing mechanical support for lead advancement. Advancing the delivery sheath 500 with the inflated balloon 505 allows for better and more accurate traversal through and in between the different septal leaflets of the tricuspid valve 125 rather than in between the chordae tendinae 110. This avoids piercing and pinning the septal leaflet of the tricuspid valve 125.

Identifying the septal attachment of the moderator band 105 also allows for identification of the trabeculum septomarginalis 135 which is a muscle bundle that runs along the long axis of the interventricular septum 107. Identifying the trabeculum septomarginalis 135 also allows for identifying yet another structure which can be used as an anatomical landmark, to make pacemaker insertion even more precise.

The structure, material, compliance, deformability, and/or the asymmetry of the balloon 505 allows the lead 155 of the medical device 150 to more accurately and safely target and be inserted into the inlet septum 117. In some examples, the curve and size of the lumen of the delivery sheath 500 and the size and shape of the asymmetric balloon 505 are preformed to facilitate insertion of the pacemaker lead 155 into the inlet septum 117.

Figure 6A:
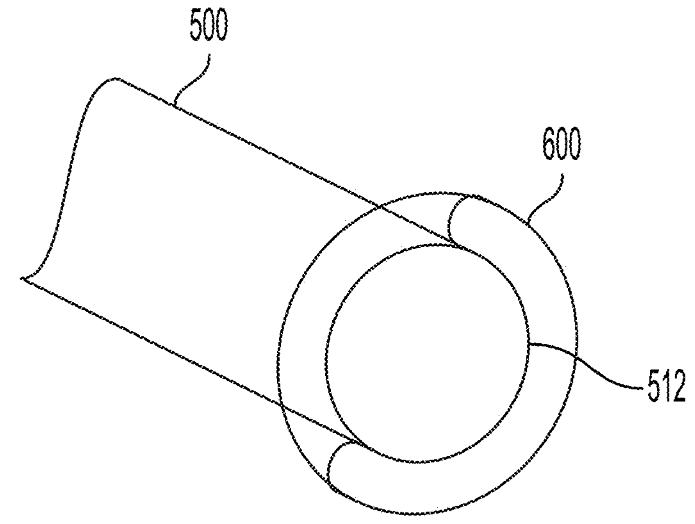
FIGS. 6A and 6B are perspective and side views of an expanded deformable distal portion of the delivery sheath having a sponge wrapped around the entire distal end of the delivery sheath to illustrate various aspects of the invention.
Figure 6B:
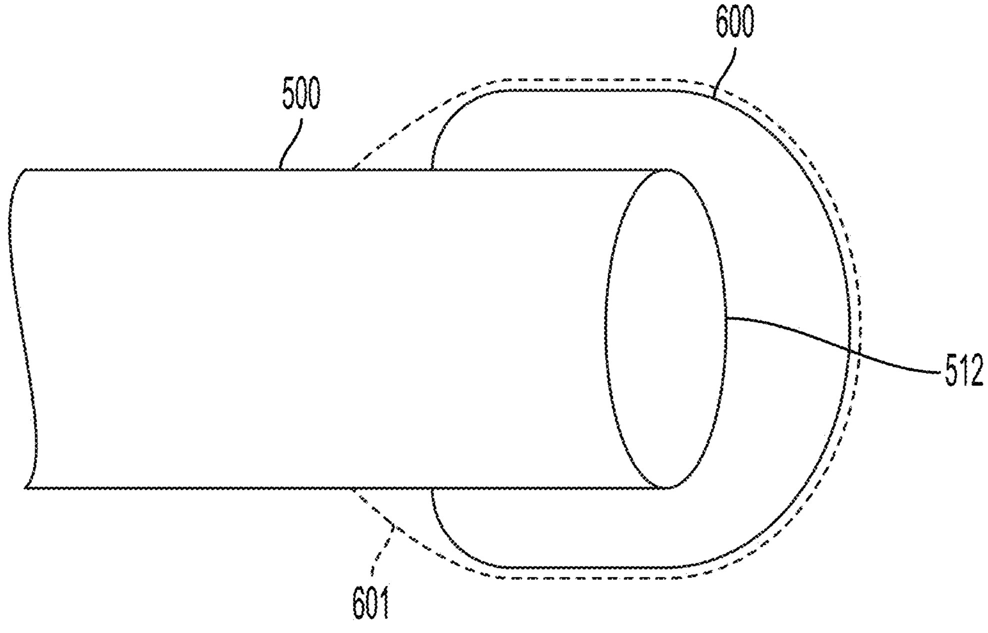

FIGS. 6A and 6B are perspective and side views of an expanded deformable distal portion 512 of the delivery sheath 500 having a sponge 600 wrapped around the entire distal end 512 of the delivery sheath 500 to illustrate various aspects of the invention. In various aspects, the sponge 600 is compressed onto the outside portion of the delivery sheath 500 and automatically expands when the sponge 600 comes out of the sheath or on contact with fluid. In various aspects, a covering 601 is placed over the sponge 600 where the expanded sponge 600 is compressed by a covering 601. The sponge 600 then expands when the outer covering 601 dissolves upon exposure to blood, thereby no longer compressing the sponge 600 and allowing it to expand. The sponge 600 expands beyond the distal end 512 of the delivery sheath 500. The sponge 600 has a maximum radial dimension (e.g., radius) that is larger than a radial dimension (e.g., a radius) of the delivery sheath 500 and is extremely deformable. In addition, the expandable portion (i.e., the sponge) may be present exclusively along the outer curvature of the delivery sheath 500 or may have an asymmetric nature in that the diameter or radial dimension is larger along the outer curvature of the delivery sheath 500.

Figure 7:
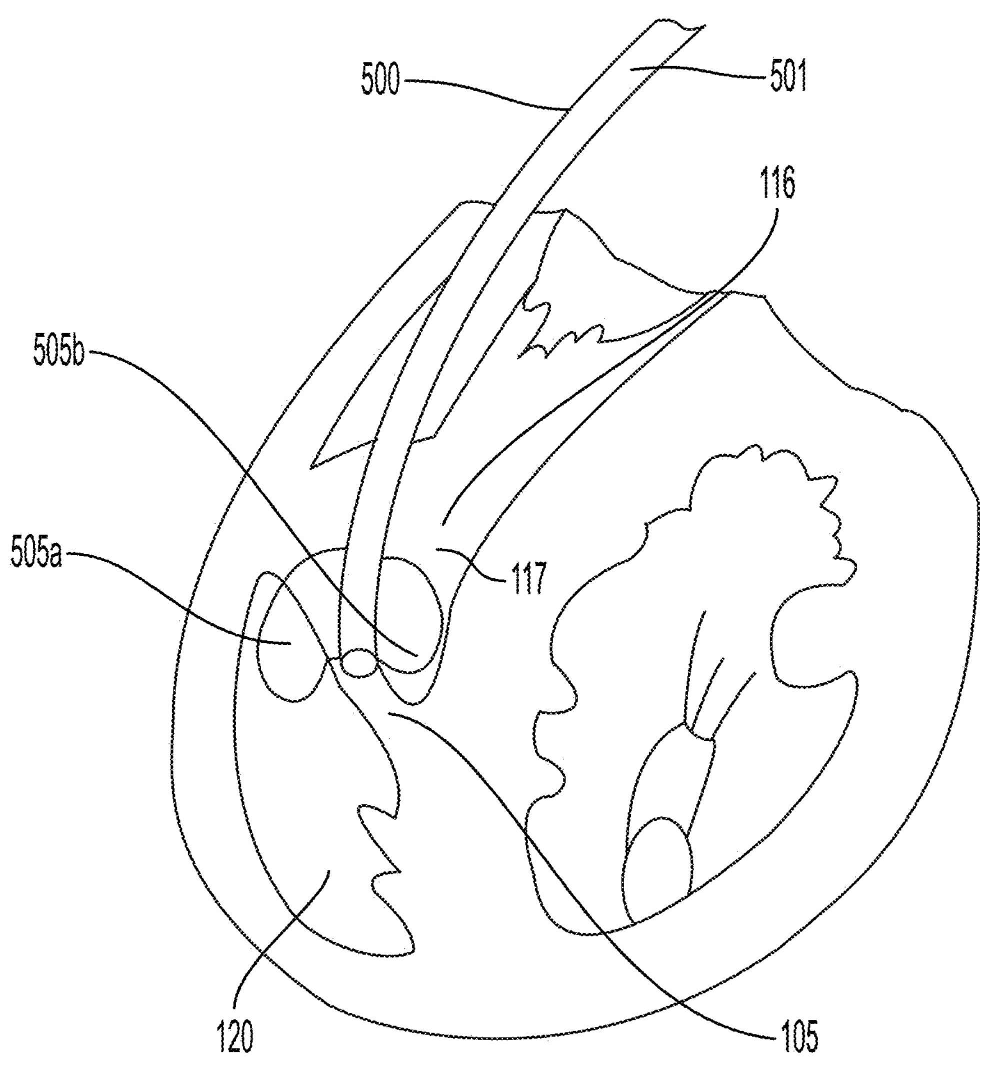
FIG. 7 is a plan view of the delivery sheath with the inflated balloon (e.g., partially or fully inflated) advanced near or into the right ventricle and is seen to indent and/or deform, indicating that it is abutting the moderator band, to illustrate various aspects of the invention.

FIG. 7 is a plan view of the delivery sheath 500 with the inflated balloon 505 (e.g., partially or fully inflated) advanced near or into the right ventricle 116 and is seen to indent and/or deform, indicating that it is abutting the moderator band 105, to illustrate various aspects of the invention. FIG. 7 also shows both the right and the left ventricular cavities separated by the interventricular septum, presumably with a left anterior oblique view. The moderator band 105 is seen to separate the smooth inlet septum 117 from the rough/uneven trabecular septum 120.

Figure 8:
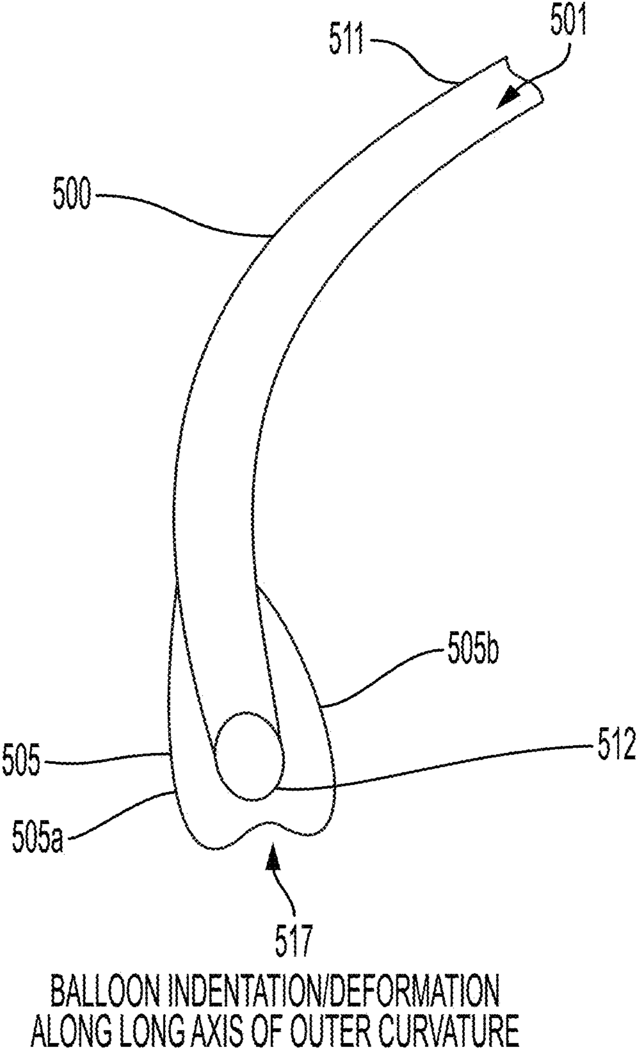
FIG. 8 is a plan view of the delivery sheath with the balloon having an indentation and/or deformation along a long axis of the outer curvature of the balloon to facilitate insertion of a lead (e.g., a pacemaker lead) into the inlet septum to illustrate various aspects of the invention.

FIG. 8 is a plan view of the delivery sheath 500 with the balloon 505 having an indentation and/or deformation 517 along a long axis of the outer curvature 514 of the balloon 505 to facilitate insertion of a lead 155 (e.g., a pacemaker lead) into the inlet septum 117 to illustrate various aspects of the invention. In this example, the delivery sheath 500 with the inflated balloon 505 (e.g., partially or fully inflated) is advanced near or into the right ventricle 116 and is seen to indent and/or deform. The indentation and/or deformation 517 of the balloon 505 along the outer curvature 514 and/or the distal pole 507 occurs along the long axis of the balloon 505. This indicates that the long axis of the delivery sheath 500 and its lumen is along the long axis of the moderator band 105. This also indicates an optimal position of the delivery sheath 500 so that it is now pointed at or against the inlet septum 117 for accurate insertion of the pacemaker lead 155.

Figure 9:
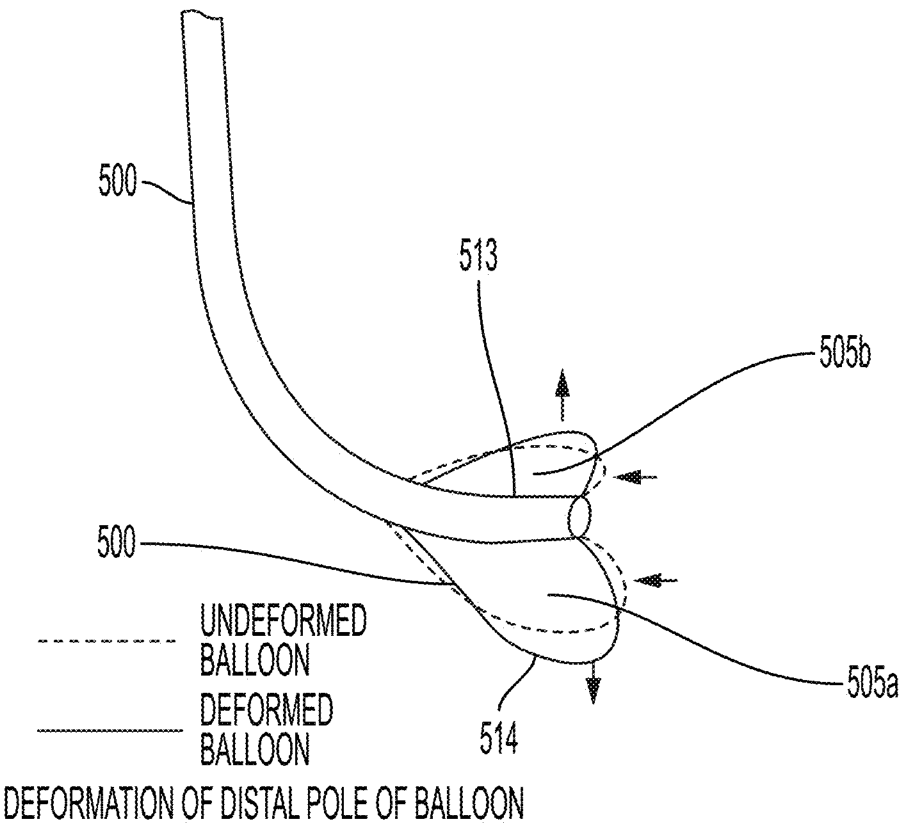
FIG. 9 is a plan view of the delivery sheath with the balloon where the balloon is shown in solid lines as a deformed balloon and in dashed lines as an undeformed balloon to illustrate various aspects of the invention.

FIG. 9 is a plan view of the delivery sheath 500 with the balloon 505 where the balloon 505 is shown in solid lines as a deformed balloon and in dashed lines as an undeformed balloon to illustrate various aspects of the invention. In this example, the delivery sheath 500 with the inflated balloon 505 (e.g., partially or fully inflated) is advanced near or into the right ventricle 116 and is seen to indent and/or deform. The indentation and/or deformation of the balloon 505 is along the distal pole 507 indicating that the balloon 505 is pushed against the inlet septum 117. As shown, the outer curvature 514 of the balloon 505 and the distal pole 507 are both deformed due to the distal pole 507 coming into contact with the inlet septum 117. This results in the distal end 512 of the delivery sheath 500 being positioned against the inlet septum 117 to allows for accurate insertion of the pacemaker lead 155.

Figure 10:
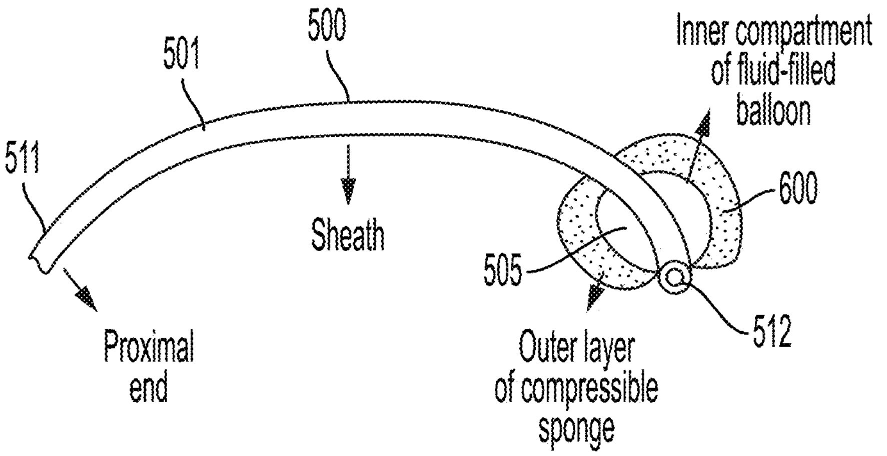
FIG. 10 is a plan view of the delivery sheath with an outer portion of the compressible sponge and an inner portion of the balloon to facilitate insertion of a lead (e.g., a pacemaker lead) into the inlet septum to illustrate various aspects of the invention.

FIG. 10 is a plan view of the delivery sheath 500 with a combination of two components such as an outer component of the compressible sponge 600 and an inner component of the balloon 505 to facilitate insertion of a lead 155 (e.g., a pacemaker lead) into the inlet septum 117 to illustrate various aspects of the invention. The compressible sponge 600 is compressed when deployed and self-expands when the sponge 600 reaches the RV 116 and/or contacts bodily fluid (e.g., blood). In this example, the inflated balloon 505 (e.g., partially or fully inflated) is positioned in the center and attached to the delivery sheath 500. The sponge 600 is positioned around the inflated balloon 505 and may be made of a material that has a contrast dye coating or radio-opaque coating. The combination is advanced near or into the right ventricle 116 and is seen to indent and/or deform when in contact with the moderator band 105. This indicates an optimal position of the delivery sheath 500 so that it is now pointed at or against the inlet septum 117 for accurate insertion of the pacemaker lead 155. In other aspects, the two components can be reversed such that the balloon 505 is the outer component and the sponge 600 is the inner component.

Figure 11:
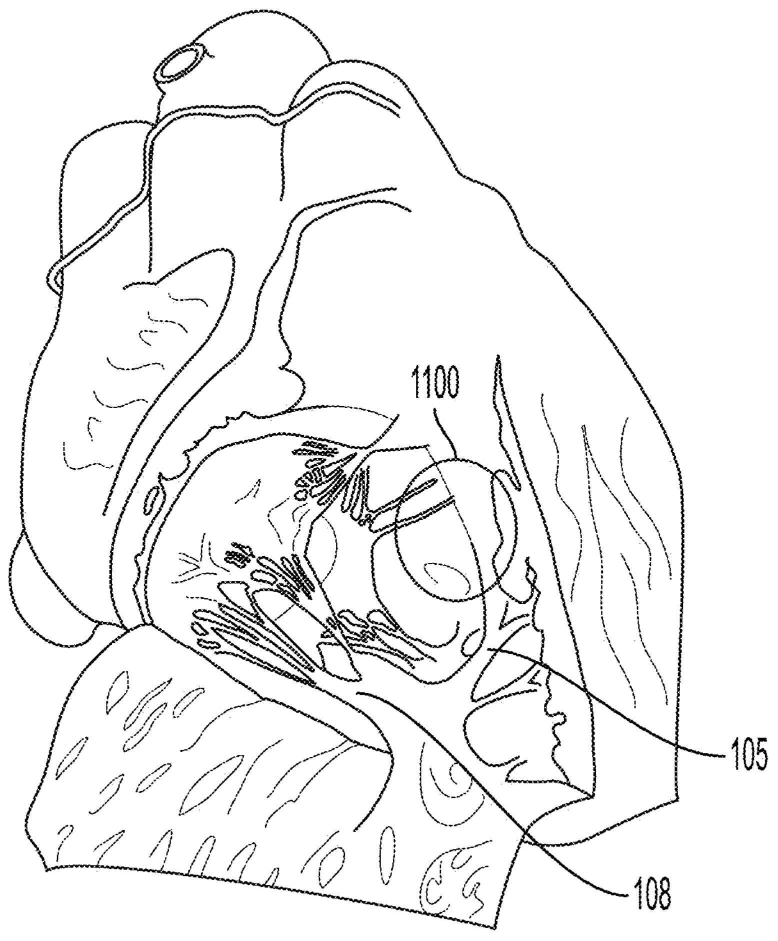
FIG. 11 shows a desired target site for lead implantation to illustrate various aspects of the invention.

FIG. 11 shows a desired target site 1100 for lead implantation to illustrate various aspects of the invention. As shown, the desired target site 1100 is next to the moderator band 105 and across from the anterior papillary muscle 108. During the medical device implantation procedure, the physician can more easily and reliably fluoroscopically identify the moderator band 105 and the anterior papillary muscle 108 using the partially or completely inflated balloon 505. That is, instead of using the tricuspid annulus, the septal attachment of the moderator band 105 is used as the anatomical landmark to guide lead placement against the ventricular septum 107.

FIG. 12 is a flowchart 1200 illustrating a method for identifying an anatomical landmark inside a human body for lead fixation of a medical device to illustrate various aspect of the invention. At step 1202, one or more of the balloons 505 are inflated using air or fluid. At 1204, a delivery sheath 500 having a distal end 512 attached to the one or more balloons 505 is advanced across a tricuspid valve 125 to a right ventricle 125. At 1206, a moderator band 105 or an anterior papillary muscle 108 is identified by the one or more balloons 505, using X-ray or fluoroscopy, by using compression or deformation of the one or more balloons 505. At 1208, the physician identifies a septal attachment of the moderator band 105 and, as a consequence, the trabeculum septomarginalis 135. The one or more balloons 505 is moved to be immediately adjacent to a smooth portion of an inlet septum 117 using the delivery sheath 500 or inflation of the one or more balloons 505 (step 1210). The lead/electrode insertion location can be made even more precise by using the trabeculum septomarginalis 135 within the inlet septum as an additional landmark. Using X-ray or fluoroscopy, compression or deformation of the one or more balloons 505 is visualized when an outer curvature and/or a distal pole of the one or more balloons contacts the inlet septum (step 1212). Using a lumen of the delivery sheath, a lead of a medical device is advanced into the inlet septum (step 1214).

In various aspects, one or more balloons are inflated using air or fluid (or the one or more balloons can be prefilled with air or fluid). The tip at the distal end of a catheter shaft, has a maximum radial dimension that is larger than the radial dimension of the catheter shaft and is extremely deformable. In addition, the expandable portion may be present exclusively along the outer curvature of the delivery sheath or may have an asymmetric nature in that the diameter or radial dimension is larger along the outer curvature of the sheath. A delivery sheath having a distal end attached to the one or more balloons is advanced across a tricuspid valve to a right ventricle. A moderator band (especially its septal attachment) or an anterior papillary muscle or the trabeculum septomarginalis is identified by the deformation of one or more balloons, using X-ray or fluoroscopy. The one or more balloons is then moved to be adjacent to a smooth portion of an inlet septum using the delivery sheath or inflation of the one or more balloons.

While the principles of the disclosure have been illustrated in relation to the exemplary embodiments shown herein, the principles of the disclosure are not limited thereto and include any modification, variation or permutation thereof.

What is claimed is:

1. A method for identifying an anatomical landmark inside a human body for lead fixation of a medical device, the method comprising:
- inflating one or more balloons using air or fluid, the one or more balloons being attached to a distal end of a delivery sheath;
- advancing the delivery sheath and the one or more balloons across a tricuspid valve to a right ventricle;
- identifying, using X-ray or fluoroscopy, a moderator band or an anterior papillary muscle of the human body;
- moving, using the delivery sheath or inflating of the one or more balloons, the one or more balloons to be adjacent to a smooth inlet septum;
- observing, using X-ray or fluoroscopy, compression or deformation of the one or more balloons when an outer curvature or a distal pole of the one or more balloons contacts the smooth inlet septum; and
- using a lumen of the delivery sheath, advancing a lead of the medical device into the smooth inlet septum.

2. The method of claim 1 wherein the one or more balloons are positioned asymmetrically with respect to the delivery sheath.

3. The method of claim 1 wherein the one or more balloons are made of a material that is compliant and deformable.

4. The method of claim 1 wherein the one or more balloons is either partially or fully inflated.

5. The method of claim 1 further comprising inserting, using a syringe, a contrast dye fluid into the one or more balloons to allow for precise and accurate identification of the anatomical landmark inside the human body.

6. The method of claim 1 wherein the one or more balloons when fully inflated do not cover or encroach on the lumen of the delivery sheath.

7. The method of claim 1 further comprising identifying, using the X-ray or the fluoroscopy, a trabeculum septomarginalis of the human body, to make advancing the lead even more precise.

8. The method of claim 1 wherein the one or more balloons is asymmetrical about the delivery sheath such that an outer portion of the one or more balloons is between 65-90% in volume and an inner portion of the one or more balloons is between 10-35% in volume for a total volume of 100% when fully inflated.

9. The method of claim 8 wherein the outer portion is larger in size and volume than the inner portion.

10. The method of claim 8 wherein the outer portion of the one or more balloons abuts, rests on or pushes against the moderator band, providing mechanical support for lead advancement.

11. A delivery system for identifying an anatomical landmark inside a human body for fixation of a lead of a medical device, the system comprising:

a delivery sheath having a proximal end and a distal end;

an inflatable balloon having an outer portion and an inner portion and being asymmetrically attached to the distal end of the delivery sheath such that the outer portion has a greater volume than the inner portion;

a self-expanding sponge attached in a compressed state to the delivery sheath or the inflatable balloon and configured to self-expand after the sponge is deployed and reaches a right ventricle of the human body or contacts bodily fluid of the human body; and an X-ray or a fluoroscopy display configured to display or identify a moderator band or an anterior papillary muscle of the human of the right ventricle;

wherein the delivery sheath is configured to be advanced across a tricuspid valve to the right ventricle, wherein the delivery sheath is configured to be moved or the inflatable balloon is configured to be inflated adjacent to a smooth inlet septum, and wherein a lead of the medical device is configured to be inserted into the smooth inlet septum.

12. The delivery system of claim 11 wherein the inflatable balloon is configured to be positioned asymmetrically with respect to the delivery sheath.

13. The delivery system of claim 11 wherein the inflatable balloon is made of a material that is compliant and deformable.

14. The delivery system of claim 11 wherein the inflatable balloon is configured to be partially or fully inflated.

15. The delivery system of claim 11 further comprising a syringe configured to insert a contrast dye fluid into the inflatable balloon to allow for precise and accurate identification of the anatomical landmark inside the human body.

16. The delivery system of claim 11 wherein the inflatable balloon when fully inflated is configured to not cover or encroach on a lumen of the delivery sheath.

17. The delivery system of claim 11 wherein the X-ray or the fluoroscopy display is configured to identify a trabeculum septomarginalis of the human, to allow more precise fixation of the lead.

18. The delivery system of claim 11 wherein the inflatable balloon is asymmetrical about the delivery sheath such that the outer portion of the inflatable balloon is between 65-90% in volume and the inner portion of the inflatable balloon is between 10-35% in volume for a total volume of 100% when fully inflated.

19. The delivery system of claim 18 wherein the outer portion of the inflatable balloon is configured to abut, rest on, or push against the moderator band to provide mechanical or structural support for lead advancement.

* * * * *